US008140467B2

United States Patent
Kasai et al.

(10) Patent No.: US 8,140,467 B2
(45) Date of Patent: Mar. 20, 2012

(54) QUANTUM STATE ESTIMATION METHOD, QUANTUM STATE ESTIMATION DEVICE AND COMPUTER PROGRAM

(75) Inventors: Hideaki Kasai, Suita (JP); Hiroshi Nakanishi, Suita (JP)

(73) Assignee: Osaka University, Osaka (JP)

( * ) Notice: Subject to any disclaimer, the term of this patent is extended or adjusted under 35 U.S.C. 154(b) by 861 days.

(21) Appl. No.: 12/280,408

(22) PCT Filed: Feb. 13, 2007

(86) PCT No.: PCT/JP2007/052483
§ 371 (c)(1),
(2), (4) Date: Aug. 22, 2008

(87) PCT Pub. No.: WO2007/097224
PCT Pub. Date: Aug. 30, 2007

(65) Prior Publication Data
US 2009/0254508 A1 Oct. 8, 2009

(30) Foreign Application Priority Data

Feb. 22, 2006 (JP) ................................. 2006-045599

(51) Int. Cl.
G06F 15/00 (2006.01)
G06F 15/18 (2006.01)
B23Q 17/09 (2006.01)
G01N 19/02 (2006.01)

(52) U.S. Cl. .......................................... 706/62; 73/104
(58) Field of Classification Search ........................ None
See application file for complete search history.

(56) References Cited

U.S. PATENT DOCUMENTS
2001/0011208 A1 8/2001 Takeuchi et al.

FOREIGN PATENT DOCUMENTS
| JP | 10232860 | 9/1998 |
| JP | 2000315633 | 11/2000 |
| JP | 2003114880 | 4/2003 |
| JP | 2003242183 | 8/2003 |

OTHER PUBLICATIONS

Kallen, Gustav et al.; "Quantum treatment of H adsorbed on a Pt(111) surface"; 2002; American Physical Socieety, Annual APS March Meeting; pp. 1-4.*
Stare, Jernej et al.; "Numerical solving of the vibrational time-dependent Schrodinger equation in one and two dimensions using the variational method"; 2002; Computer Physics Communications, vol. 143, Issue 3; pp. 222-240 (1-19).*
McCreery, Jane Hylton et al.; "A model potential for chemisorption: H2 + W(001)"; 1975; The Journal of Chemical Physics, vol. 63, No. 6; pp. 2340-2349 (1-11).*

(Continued)

*Primary Examiner* — Jeffrey A Gaffin
*Assistant Examiner* — Stanley K Hill
(74) *Attorney, Agent, or Firm* — Katten Muchin Rosenman LLP

(57) ABSTRACT

A control section virtually divides a surface of an adsorbing material into a plurality of regions (cells) in accordance with a computer program. Further, the control section-allocates a normal distribution function to each of the divided cells, and sets a linear combination of the normal distribution functions allocated to all cells to a trial function. Moreover, the control section solves a Schrödinger equation based upon a potential on the surface of the adsorbing material by a numerical variational method, to calculate a wave function. Then, based upon the calculated wave function, the quantum state of the atom or the molecule adsorbed on the surface of the adsorbing material is estimated.

13 Claims, 10 Drawing Sheets

OTHER PUBLICATIONS

International Search Report dated Mar. 13, 2007 from the corresponding PCT/JP2007/052483.

Kohn, W. et al. "Self-Consistent Equations Including Exchange and Correlation Effects" Physical Review, vol. 140, No. 4A, p. 1133-1138, Nov. 15, 1965.

Hohenberg, P. et al., "Inhomegenous Electron Gas" Physical Review, vol. No. 136, No. 3B, p. 864-871, Nov. 9, 1964.

Nobuhara, K. et al., "Quantum mechanical behavior of an H atom on Cu(111) and Pt(111)" Journal of Applied Physics, vol. 91, No. 4, p. 1855-1859, Feb. 15, 2002.

* cited by examiner

F I G. 1
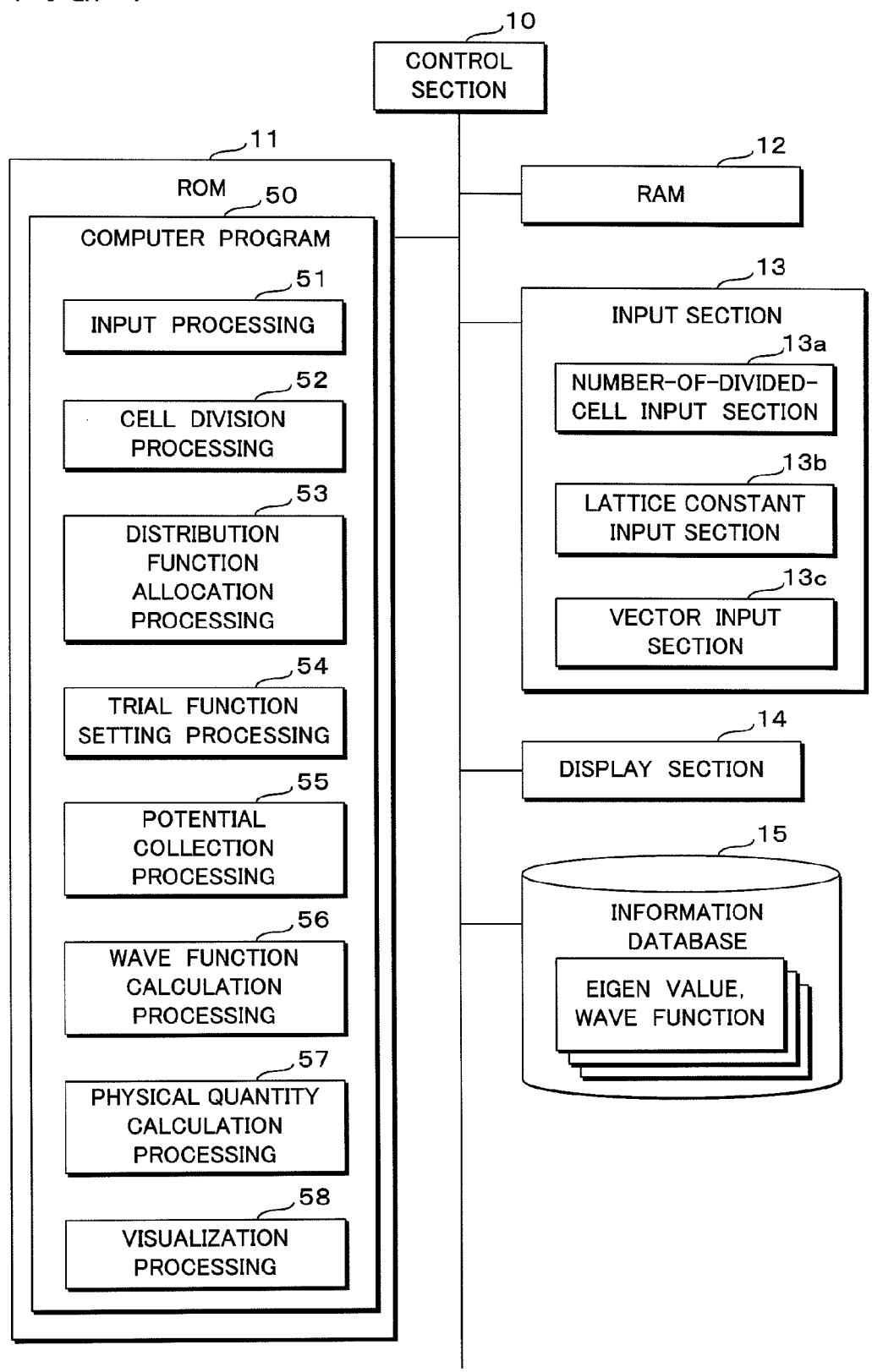

F I G. 3

| ID | Cx | Cy | Cz |
|---|---|---|---|
| 1 | 1 | 1 | 1 |
| 2 | 1 | 1 | 2 |
| ⋮ | ⋮ | ⋮ | ⋮ |
| 5 | 1 | 1 | 5 |
| 6 | 1 | 2 | 1 |
| 12 | 1 | 2 | 2 |
| ⋮ | ⋮ | ⋮ | ⋮ |
| 10 | 1 | 2 | 5 |
| ⋮ | ⋮ | ⋮ | ⋮ |
| 316 | 8 | 8 | 1 |
| 317 | 8 | 8 | 2 |
| ⋮ | ⋮ | ⋮ | ⋮ |
| 320(N) | 8 | 8 | 5 |

FIG. 5

| | j | EIGEN VALUE $E_j$ | WAVE FUNCTION $\Psi_j$ | | | | |
|---|---|---|---|---|---|---|---|
| | | | $A_1$ | $A_2$ | $A_3$ | ... | $A_N$ |
| GROUND STATE | 0 | | | | | | |
| FIRST EXCITED STATE | 1 | | | | | | |
| SECOND EXCITED STATE | 2 | | | | | | |
| THIRD EXCITED STATE | 3 | | | | | | |

QUANTUM STATE ESTIMATION METHOD, QUANTUM STATE ESTIMATION DEVICE AND COMPUTER PROGRAM

This application is the national phase under 35 U.S.C. §371 of PCT International Application No. PCT/JP2007/52483 which has an International filing date of Feb. 13, 2007 and designated the United States of America.

BACKGROUND

1. Technical Field

The present invention relates to a quantum state estimation method, a quantum state estimation device and a computer program for estimating a quantum (movement) state of an atom or a molecule adsorbed on a surface of a material, and particularly relates to a quantum state estimation method, a quantum state estimation device and a computer program for realizing the quantum state estimation method by means of a computer, that are preferable in a case where an object is hydrogen (including light hydrogen, deuterium, and tritium) or a lithium, which has a small mass and whose quantum effect appears remarkably.

2. Description of Related Art

In recent years, attention has been focused on hydrogen as an alternative energy source to a fossil fuel such as oil in an attempt to deal with global environment problems such as ozone layer destruction and air pollution. A representative example of the use of hydrogen is a fuel cell, in which an easily oxidizable fuel such as hydrogen is reacted with oxygen rich in the atmosphere, and chemical energy generated through the chemical reaction is not converted into heat, but directly converted into electric energy. Further, when hydrogen is used as the fuel, a product of the reaction with oxygen is water alone, and hence there is in no danger of leading to environmental destruction, and hydrogen has thus been considered to serve as a mainstream energy in the future.

Incidentally, palladium, Pd is capable of absorbing hydrogen in large amount, whereas nickel, Ni generates hydride only at high pressure, and platinum, Pt just allows hydrogen to penetrate and is not capable of absorbing hydrogen in large amount. As thus described, since nickel, Ni, palladium, Pd and platinum, Pt have different hydrogen storage characteristics although all belonging to group 10 metal, it is necessary to consider a behavior of hydrogen as an adsorbed atom due to an inherent potential that is formed in accordance with each atom.

The potential is obtained in such a manner that an adsorbed atom is arranged on the surface, a total energy (excluding kinetic energy of the adsorbed atom) as a function of a coordinate of the atom is obtained by a first principle calculation based upon a density functional method (e.g. see "Physical Review", issued on Nov. 9, 1964, Volume No. 136, p. 864-871 and "Physical Review", issued on Nov. 15, 1965, Volume No. 140, p. 1133-1138), and a hypersurface of a potential energy for the atom on the surface (which is a curve, a curved surface or a hypersurface depending upon a dimension, but here, it is regarded as a hypersurface in the case of a two or larger dimensions) is derived. From the view point of classical mechanics, a coordinate of the atom corresponding to an energy minimum point of the derived potential curved surface is at the adsorption position, and a value, obtained by dividing a partial differential coefficient of second order by a mass of the atom on a coordinate in a specific direction around the energy minimum point, calculating a square root of the obtained value, and multiplying the square root by Dirac constant h/2π, provides vibrational energy.

However, when the atom has a small mass, the quantum effect appears remarkably, and the minimum point of the potential curved surface is not necessarily the adsorption position. Further, in the case of a metal surface, typically, a non-harmonic characteristic of the potential curved surface is distinguished, and when the non-harmonic characteristic of the potential curved surface is distinguished, the square root of the partial differential coefficient of second order is not proportional to the vibrational energy. Further, an effect of finite zero-point energy exists.

This is because, in the quantum world, a material has bilateral characteristics of a particle and a wave, and the wave characteristic is distinguished especially on a microscopic scale. Therefore, in order to accurately grasp the quantum state of the adsorbed atom, it is necessary to solve a Schrödinger equation [Formula (1)] so as to calculate a wave function Ψ. In Formula (1), "m" is a mass of an adsorbed atom, "h" is a Planck's constant (note: "h/2π" is a Dirac constant), "V" is a potential energy, and "$E_j$" is eigen energy (characteristic value), and an eigen wave function $\Psi_j$ corresponds to each eigen value $E_j$.

$$\left\{-\frac{\left(\frac{h}{2\pi i}\right)^2}{2m}\nabla^2 + V(x, y, z)\right\} f\mu_j(x, y, z) = E_j f\mu_j(x, y, z),$$

$$\text{where } \nabla^2 = \left(\frac{\partial^2}{\partial x^2} + \frac{\partial^2}{\partial y^2} + \frac{\partial^2}{\partial z^2}\right).$$

Formula (1)

Since the quantum states of the atom that is adsorbed are decided in accordance with the potential V formed by the adsorbing material, for example when the interaction between the adsorbed atom and the adsorbing material is strong and a deep potential is formed, the adsorbed atom is adsorbed on the surface of the adsorbing material in its stable state, and is thus not easily desorbed from the adsorbing material. Hence it is considered essential for enhancement of the hydrogen storage technique to realize the technique for highly accurately estimating quantum states of an atom or a molecule that is adsorbed.

SUMMARY

However, it has been difficult to analytically solve the eigen value $E_j$ and the eigen wave function $\Psi_j$ depending upon the potential V, and thereby extremely difficult to estimate a quantum state of an atom or a molecule which has a small mass and whose quantum effect appears remarkably, such as hydrogen. Further, it has also been difficult to measure quantum states of an atom or a molecule such as hydrogen on a solid surface experimentally, and there has thus been a demand for a technique for highly accurately estimating quantum states of an atom or a molecule adsorbed on a surface of a material.

The present invention was made in view of such circumstances, and an object thereof is to provide a quantum state estimation method and a quantum state estimation device in which a surface of an adsorbing material of an atom is first virtually divided into a plurality of regions, a normal distribution function is then allocated to each of the divided regions, a linear combination of the normal distribution functions allocated to all regions is set to a trial function, a Schrödinger equation based upon a potential on the surface of the adsorbing material is solved by a numerical variational method, to calculate a wave function, and a quantum state of an atom or a molecule adsorbed on the surface of the adsorbing material is estimated based on the calculated wave function, so that the wave function can be calculated with high accuracy even in the case of the potential being complex, and the estimation accuracy of the quantum state of the adsorbed atom or the adsorbed molecule can be improved.

Further, an object of the present invention is to provide a quantum state estimation method and a quantum state estimation device in which a potential is corrected based upon translational symmetry and/or rotational symmetry of an atom or a molecule on a surface of an adsorbing material, so that the accuracy of the potential on the surface of the adsorbing material can further be improved, and the quantum states of the atom or the molecule adsorbed on the surface of the adsorbing material can be estimated with higher accuracy.

Moreover, an object of the present invention is to provide a computer program for realizing a function as the quantum state estimation device as described above by means of a computer.

A quantum state estimation method according to a first aspect is a quantum state estimation method for estimating quantum states of an atom or a molecule adsorbed on a surface of a material based upon a potential on the surface of the material, characterized in that the surface of the material is virtually divided into a plurality of regions, a normal distribution function is allocated to each of the divided regions, a Schrödinger equation based upon the potential on the surface of the material is solved by a numerical variational method with a linear combination of the normal distribution functions allocated to all regions as a trial function is solved, to calculate a wave function, and the quantum state of the atom or molecule is estimated based upon the calculated wave function.

A quantum state estimation method according to a second aspect is characterized in that in the first aspect, the potential is corrected by superimposing potentials after symmetry operations performed based upon translational symmetry and/or rotational symmetry of the atom or molecule on the surface of the material upon a potential before the symmetry operation.

A quantum state estimation method according to a third aspect is characterized in that in the first aspect or the second aspect, a Morse potential type in the perpendicular direction to the surface is assumed as the potential, and structural parameters of the Morse potential at a position, where the center of each region is projected to the surface, are calculated.

A quantum state estimation method according to a forth aspect is characterized in that in any one of the first aspect to the third aspect, a region is decided in which the surface of the material is divided based upon an array periodicity of an atom constituting the material.

A quantum state estimation device according to a fifth aspect is a quantum state estimation device for estimating a quantum state of an atom or a molecule adsorbed on a surface of a material based upon a potential on the surface of the material, characterized by comprising: means for virtually dividing the surface of the material into a plurality of regions; means for setting a linear combination of normal distribution functions with respect to all of the divided regions to a trial function; and means for solving a Schrödinger equation based upon the potential on the surface of the material by a numerical variational method on the basis of the set trial function, to calculate a wave function.

A quantum state estimation device according to a sixth aspect is characterized in that in the fifth aspect, the device further comprises means for correcting the potential based upon translational symmetry and/or rotational symmetry of the atom or molecule on the surface of the material.

A computer program according to a seventh aspect is a computer program for causing a computer to estimate a quantum state of an atom or a molecule adsorbed on a surface of a material provided with a lattice constant based upon a potential on the surface of the material, comprising the steps of: causing the computer to virtually divide the surface of the material into a plurality of regions based upon the lattice constant; causing the computer to allocate a normal distribution function to each of the divided regions; causing the computer to set a linear combination of normal distribution functions allocated to all regions to a trial function; and causing the computer to solve a Schrödinger equation based upon the potential on the surface of the material by a numerical variational method on the basis of the set trial function, to calculate a wave function.

A computer program according to an eighth aspect is characterized in that in the seventh aspect, the program further comprises the step of causing the computer to correct the potential based upon translational symmetry and/or rotational symmetry of the atom or molecule on the surface of the material.

A computer program according to a ninth aspect is characterized in that in the seventh aspect or the eighth aspect, the program further comprises the step of causing the computer to calculate a physical quantity for specifying the quantum state based upon the wave function.

A computer program according to a tenth aspect is characterized in that in the ninth aspect, the wave functions are a plurality of functions corresponding respectively to a plurality of eigen values, and the program further comprises the steps of: causing the computer to store the plurality of functions; and causing the computer to select and read a function required for calculating the physical quantity out of the plurality of functions.

A computer program according to an eleventh aspect is characterized in that in any one of the seventh aspect to the tenth aspect, the program further comprises the step of causing the computer to visualize the physical quantity.

In the first aspect, the fifth aspect and the seventh aspect, first, a surface of an adsorbing material of an atom is virtually divided into a plurality of regions. Subsequently, a normal distribution function is allocated to each of the divided regions, and a linear combination of the normal distribution functions allocated to all regions is set to a trial function. A Schrödinger equation based upon a potential on the surface of the adsorbing material is solved by a numerical variational method, to calculate a wave function. Then, a quantum state of an atom or a molecule adsorbed on the surface of the absorbing material is estimated based upon the calculated wave function. This prevents neglect of contribution to the adsorbed atom or the adsorbed molecule from the potential in each region, thereby to improve the estimation accuracy of the quantum state of the adsorbed atom or the adsorbed molecule. Further, with the use of numerics named the numerical variational method, the wave function can be calculated even in the case of the potential being complex.

In the second aspect, the sixth aspect and the eighth aspect, a potential is corrected based upon translational symmetry and/or rotational symmetry of an atom or a molecule on a surface of an adsorbing material. It is thereby possible to improve the accuracy of the potential on the surface of the adsorbing material, and highly accurately estimate the quantum state of the atom or the molecule adsorbed on the surface of the adsorbing material.

In the third aspect, a Morse potential type in the perpendicular direction to a surface of an adsorbing material is assumed as the potential on the surface, and a structural parameter of the Morse potential at a position where the center of each divided region is projected to the surface is calculated. In the case of the potential being complex, it is extremely difficult to analytically solve the Schrödinger equation, and the equation is algebraically solved by numerics. Although the Morse potential was made for describing a potential of two-particle interaction, it is preferred as an adsorption potential on a surface of a metal handled in the present invention.

In the fourth aspect, a region is decided in which the surface of the adsorbing material is divided based upon an array periodicity of an atom constituting the adsorbing material. An array of an atom constituting the adsorbing material such as a metal surface has a periodicity, and by deciding a region to be divided based upon the periodicity of the atom, it is possible to perform some calculation processes on a unit based upon the periodicity, so as to reduce the calculation cost.

In the ninth aspect, a physical quantity for specifying a quantum state of an atom or a molecule adsorbed on a surface of a material is calculated based upon a wave function. Since the quantum state of the atom or the molecule is decided based upon the wave function, it is possible to calculate a probability distribution, a momentum distribution, and the like of each quantum state, by means of the wave function.

In the tenth aspect, calculated wave functions are a plurality of functions corresponding respectively to a plurality of eigen values, the calculated plurality of functions are stored, and a function required for calculating a physical quantity to specify a quantum state of an atom or molecule adsorbed on a surface of a material is appropriately selected and read out of the plurality of stored functions. For example, when a ground state of an adsorbed atom or molecule is wished to be grasped, an eigen value and a wave function in the ground state have only to be selected and read, and a physical quantity in the ground state has only to be calculated from the read eigen value and wave function. Further, in the case of calculating energy that is radiated in state transition from an excited state to the ground state, an eigen value in the ground state and an eigen value in the excited state are selected and read, and subtraction of the read eigen values is performed, so as to easily obtain radiant energy.

In the eleventh aspect, after calculation of a physical quantity for specifying a quantum state of an atom or molecule adsorbed on a surface of a material, the calculated physical quantity is visualized. Since the physical quantity is not expressed by mere aggregation of numerical data but is visualized, it is possible for a user to easily grasp the quantum state of the atom or the molecule by viewing the visualized image.

According to the present invention, a surface of an adsorbing material of an atom is first virtually divided into a plurality of regions, a normal distribution function is then allocated to each of the divided regions, a linear combination of the normal distribution functions allocated to all regions is set to a trial function, a Schrödinger equation based upon a potential on the surface of the adsorbing material is solved by a numerical variational method, to calculate a wave function, and a quantum state of an atom or a molecule adsorbed on the surface of the adsorbing material is estimated based upon the calculated wave function, thereby preventing neglect of contribution to the adsorbed atom or the adsorbed molecule from the potential in each region, so as to improve the estimation accuracy of the quantum states of the adsorbed atom or the adsorbed molecule. Further, with the use of numerics named the numerical variational method, the wave function can be calculated even in the case of the potential being complex, and hence applications are versatile.

According to the present invention, a potential is corrected based upon translational symmetry and/or rotational symmetry of an atom or a molecule on a surface of an adsorbing material, so that the accuracy of the potential on the surface of the adsorbing material can further be improved, and the quantum state of the atom or the molecule adsorbed on the surface of the adsorbing material can be estimated with higher accuracy.

According to the present invention, a Morse potential type in the perpendicular direction to a surface of an adsorbing material is assumed as the potential on the surface, and structural parameters of the Morse potential at each position where the center of each divided region is projected to the surface is calculated. Although the Morse potential is made for describing a potential of two-particle interaction, it is preferred as an adsorption potential on a surface of a metal handled in the present invention.

According to the present invention, a region is decided in which the surface of the adsorbing material is divided based upon an array periodicity of an atom constituting the adsorbing material, and thereby it is possible to perform some calculation processes on a unit based upon the periodicity, so as to reduce the calculation cost.

According to the present invention, a physical quantity for specifying a quantum state of an atom or a molecule adsorbed on a surface of a material is calculated based upon a wave function. Since the quantum state of the atom or the molecule is decided based upon the wave function, it is possible to calculate a probability distribution, a momentum distribution, and the like of each quantum state by means of the wave function.

According to the present invention, calculated wave functions are a plurality of functions corresponding respectively to a plurality of eigen values, the calculated plurality of functions are stored, and a function required for calculating a physical quantity to specify a quantum state of an atom or molecule adsorbed on a surface of a material is appropriately selected and read out of the plurality of stored functions. For example, when a ground state of an adsorbed atom or molecule is wished to be grasped, an eigen value and a wave function in the ground state have only to be selected and read, and a physical quantity in the ground state has only to be calculated from the read eigen value and wave function. Further, in the case of calculating energy that is radiated in state transition from an excited state to the ground state, an eigen value in the ground state and an eigen value in the excited state are selected and read, and subtraction of the read eigen values is performed, so as to easily obtain radiant energy.

According to the present invention, after calculation of a physical quantity for specifying a quantum state of an atom or molecule adsorbed on a surface of a material, the calculated physical quantity is visualized. Since the physical quantity is not expressed by mere aggregation of numerical data but is visualized, it is possible for a user to easily grasp the quantum state of the atom or the molecule by viewing the visualized image.

Accordingly, it is possible to estimate an adsorption site, a vibration mode and the like based upon information obtained by the present invention, such as a wave function and an eigen value, and such estimation is extremely effective in development of a catalyst associated with hydrogen, and research and development of surface treatment and the like. Further, an electronic device focusing on controlling a behavior of an electron is currently under development, and with the use of the present invention, an excellent effect is exerted such as an effect of grasping a complex behavior of an atom with high accuracy to create an effective technique for the development of an atomic device that controls the behavior of the atom.

The above and further objects and features will more fully be apparent from the following detailed description with accompanying drawings.

BRIEF DESCRIPTION OF THE SEVERAL VIEWS OF THE DRAWINGS

FIG. 1 is a block diagram showing a configuration of a quantum state estimation device according to the present invention.

FIG. 3 is a view showing an example of information of divided cells.

FIG. 5 is a view showing an overview of an eigen value and a wave function.

DETAILED DESCRIPTION

Figure 2:
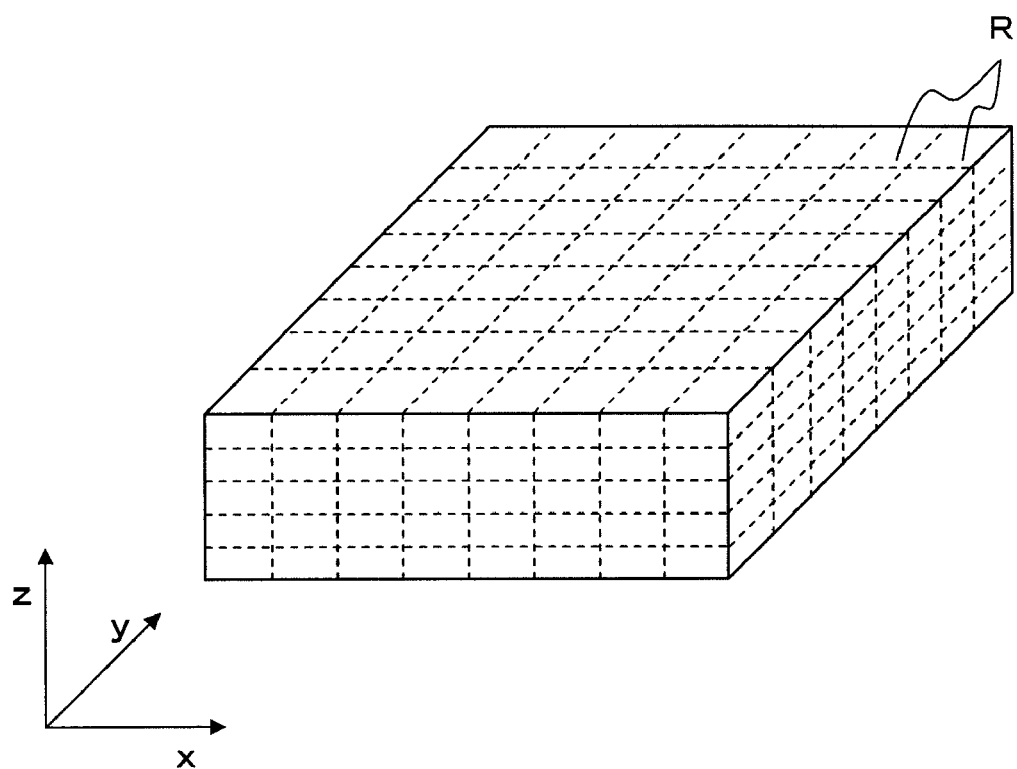
FIG. 2 is a schematic view showing an overview of cell setting processing.

In the following, the present invention is detailed based upon drawings showing embodiments thereof.

FIG. 1 is a block diagram showing a configuration of a quantum state estimation device according to the present invention.

The quantum state estimation device according to the present invention has a control section 10 configured of a CPU. The control section 10 is connected with a ROM 11, a RAM 12, an input section 13, a display section 14, information database 15 and the like, and functions as a variety of means according to the present invention in cooperation with the respective sections in accordance with a computer program 50 previously stored in the ROM 11. The RAM 12 stores temporary data generated at the time of execution of a computer program by the control section 10, and is configured of a semiconductor memory such as a DRAM.

The computer program 50 stored in the ROM 11 includes a program for performing: input processing 51 for accepting inputs of a lattice constant L of an adsorbing material, a Bravais vector in the parallel direction to a surface of the adsorbing material, and a perpendicular vector in the perpendicular direction to the surface of the adsorbing material; cell division processing 52 for virtually dividing the surface of the absorbing material into a plurality of regions (cells) based upon the accepted lattice constant L, Bravais vector and perpendicular vector; distribution function allocation processing 53 for allocating a normal distribution function to each of the divided cells; trial function setting processing 54 for setting a linear combination of normal distribution functions allocated to all cells to a trial function; potential collection processing 55 for correcting a potential based upon translational symmetry and rotational symmetry of an atom on the surface of the adsorbing material; and wave function calculation processing 56 for solving a Schrödinger equation based upon the potential on the surface of the adsorbing material by a numerical variational method on the basis of the set trial function, to calculate a wave function.

Also included is a program for further performing: physical quantity calculation processing 57 for calculating a physical quantity for specifying a quantum state based upon the calculated wave function; and visualization processing 58 for visualizing the calculated physical quantity. The physical quantity, for example, is a momentum of the adsorbed atom, a quantity of energy reflected or absorbed with the state transition, or the like.

Further, since a plurality of wave functions become solutions of the Schrödinger equation in correspondence with a plurality of respective eigen values, processing is included in the computer program for storing a plurality of wave functions, and selecting and reading a wave function required for calculating a physical quantity, out of the plurality of wave functions.

The input section 13 serves to input a variety of parameters in calculation of the potential on the surface of the material, and has: a number-of-divided-cells input section 13$a$, a lattice constant input section 13$b$, a vector input section 13$c$, and the like. The cells in the present invention refer to a plurality of blocks into which the surface of the adsorbing material is virtually divided, and from the user, the number-of-divided-cells input section 13$a$ accepts the number of divided cells, the lattice constant input section 13$b$ accepts a lattice constant L of the adsorbing material, and the vector input section 13$c$ accepts a Bravais vector in the parallel direction to the surface of the adsorbing material and a perpendicular vector in the perpendicular direction to the surface.

In the case of accepting the number of cells, the lattice constant L of the adsorbing material, the Bravais vector and the perpendicular vector in the input section 13, the control section 10 virtually divides a space on the surface of the adsorbing material into cells in accordance with the accepted number of cells, lattice constant L of the adsorbing material, Bravais vector and perpendicular vector. For example in a case where an x-axis and a y-axis are Bravais vectors, a z-axis is a perpendicular vector, the number of divided cells in each of the directions of the Bravais vectors is 8 and the number of divided cells in the direction of the perpendicular vectors is 5, as shown in FIG. 2, the space on the external side of the surface of the adsorbing material is virtually divided into a plurality of cells R [8×8×5=320 (N)].

Then, as for information on the divided cells, an identification number (ID) for identifying a cell is allocated to each cell, and thereafter, as shown in FIG. 3, ID, a cell number Cx in the x-direction, a cell number Cy in the y-direction, and a cell number Cz in the z-direction are stored into the RAM 12. It is to be noted that, since later-described calculation time is decided based upon the number of divided cells, the number of cells is appropriately set in accordance with kinds, configurations and the like of the adsorbed atoms and the adsorbing material.

Subsequently, the control section 10 allocates a three-dimensional normal distribution function [Formula (2)] to each divided cell based upon the cell information, and sets a linear combination of the normal distribution functions allocated to all cells to a trial function [Formula (3)].

$$\exp\left(-f\dot{A}1\{(x-X_i)^2+(y-Y_i)^2\}-f\dot{A}2(z-Z_i)^2\right), \quad \text{Formula (2)}$$

$$f\mu(x,y,z) = \sum_i A_i \exp\left(-f\dot{A}1\{(x-X_i)^2+(y-Y_i)^2\}-f\dot{A}2(z-Z_i)^2\right). \quad \text{Formula (3)}$$

In Formula (2), β1 is a parameter representing expansion of the normal distribution in the x-direction and the y-direction, 132 is a parameter representing expansion of the normal distribution in the z-direction, $X_i$, $Y_i$ and $Z_i$ are a coordinate of a central position of an i-th [i=1 to N (number of divided cells)] cell. Further, in Formula (3), a coefficient $A_i$ is a contribution ratio to a wave function Ψ from i-th cell.

Figure 4:
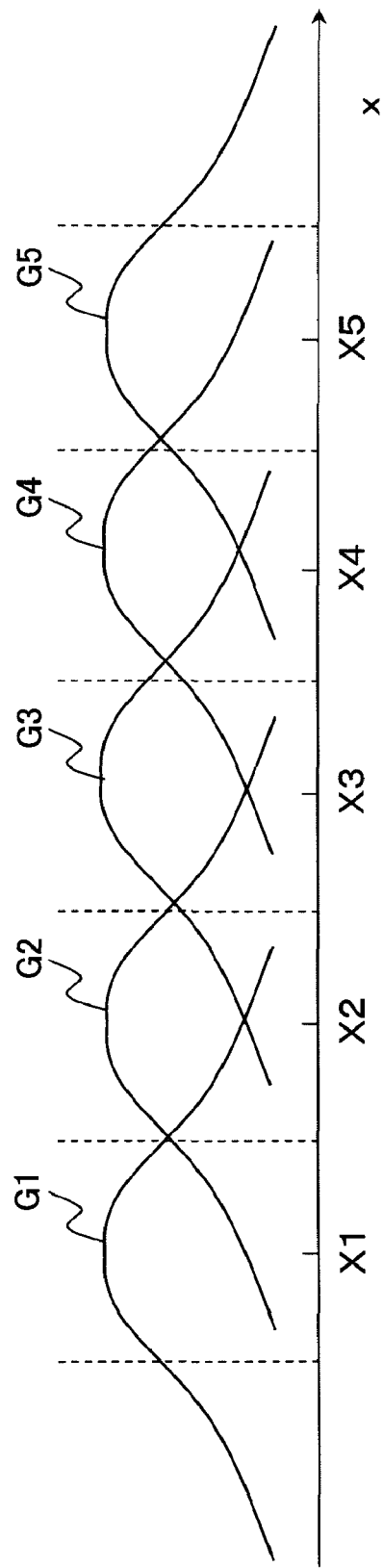
FIG. 4 is a view showing an overview of a trial function.

When a description is made in the case of one dimension for easier comprehension, as shown in FIG. 4, a linear combination of normal distributions G1, G2, . . . with the central positions X1, X2, . . . of the respective cells positioned at the centers is set to a trial function.

Then, the control section 10 performs processing for correcting a potential based upon translational symmetry and rotational symmetry of the atom on the surface of the adsorbing material, and thereafter solves the Schrödinger equation based upon the potential on the surface of the material by a numerical variational method with respect to the set trial function, to calculate a wave function.

In the present example, in solving the Schrödinger equation, a Morse potential type [Formula (4)] is assumed in the perpendicular direction to the surface as the potential, and parameters $D(x_i, y_i)$, $\beta(x_i, y_i)$ and $Z_0(x_i, y_i)$ of the Morse potential at a position $(x_i, y_i)$ projected to the surface of the center of each cell are obtained by a first principles calculation based upon a density functional method.

$$V(x_i,y_i,z_i)=D(x_i,y_i)[\{\exp(-f\dot{A}(x_i,y_i)(z-Z_0(x_i,y_i)))-1\}^2-1]. \quad \text{Formula (4)}$$

In Formula (4), $D(x_i, y_i)$ is a depth of a potential well at the position $(x_i, y_i)$, $\beta(x_i, y_i)$ is a curvature describing a curving degree of a potential curve, and $Z_0(x_i, y_i)$ is a position of the potential well in the perpendicular direction to the surface.

Although the Morse potential is made as a potential of two-particle interaction, it is preferred as an adsorption potential on a surface of a metal. Not only one solution but a plurality of solutions (eigen value $E_j$) of the Schrödinger equation exist, and each eigen value E; and an eigen wave function Ψ with respect to each eigen value $E_j$ are calculated as a pair. It should be noted that in the present example, the size of the cells in the X-direction and the Y-direction on the surface of the adsorbing material is set to be same, and the Schrödinger equation is then solved using the identical parameter β for both of the X-direction and the Y-direction, thereby the calculation cost is reduced.

The calculated eigen value $E_j$ and wave function $\Psi_j$ are stored into the information database 15 (FIG. 5). Here, an eigen value $E_0$ is an eigen value in the ground state, and $\Psi_0$ is a wave function in the ground state. Further, eigen values $E_1$, $E_2$, $E_3$, . . . ($E_0 \leq E_1 \leq E_2 \leq E_3$ . . . ) are eigen values . . . in a first excited state, a second excited state, a third excited state, . . . , and $\Psi_1$, $\Psi_2$, $\Psi_3$, . . . are wave functions in the respective excited states. The wave function Ψ is given by a trial function set as in Equation (3), and $\Psi_i$ is specified by a coefficient $A_i$ of the normal distribution function.

Figure 6:
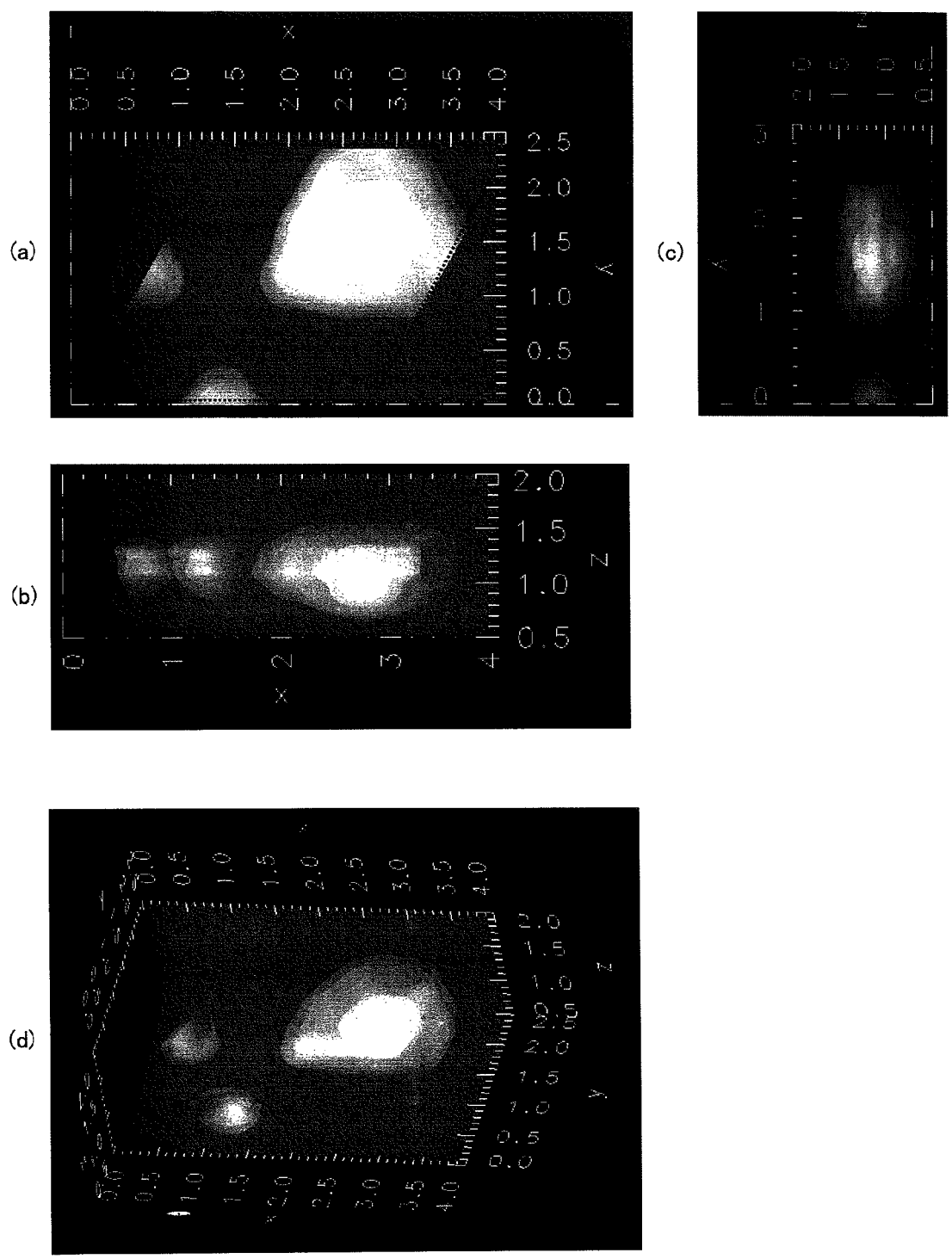
FIG. 6 is an image showing an example of a probability distribution of an adsorbed atom.

Since a square value of the calculated wave function represents a probability distribution of the adsorbed atom, the value is imaged using a known imaging tool as shown in FIG. 6 and then displayed in the display section 14 so that the user can accurately grasp the probability distribution of the adsorbed atom with respect to the position from the image displayed in the display section 14. It is to be noted that in FIG. 6, a probability distribution of a hydrogen atom on a surface of platinum (111) is shown, where (a) is a plan view (x-y plane), (b) is a front view (x-z plane), (c) is a side view (y-z plane), and (d) is a bird's-eye view, and a scale is A.

Next, as an example of a physical quantity that specifies the quantum state of the absorbed atom, a momentum of the absorbed atom is calculated using the wave function calculated in the manner as described above. The calculated momentum of the absorbed atom is imaged using the known imaging tool so as to allow grasping of a momentum distribution and then displayed in the display section 14 (cf. FIG. 9 etc.). Thereby, from the momentum distribution image displayed in the display section 14, the user can accurately grasp a state in which the absorbed atom is adsorbed on the surface of the adsorbing material.

In the manner as thus described, even in the case of the potential in a complex shape, it is possible by numerics named the numerical variational method to calculate an eigen value and a wave function describing a quantum state of an atom or molecule adsorbed on a surface of a material. In the present invention, since the normal distribution function is allocated to the center of each divided cell, it is possible to prevent neglect of contribution to the adsorbed atom from the potential in each cell, so as to improve the accuracy of the quantum state of the adsorbed atom. Accordingly, it is possible to accurately calculate a physical quantity such as a momentum distribution based upon each calculated eigen value and a wave function corresponding to that eigen value, and further to accurately and clearly grasp the physical quantity by visualizing the physical quantity and displaying the visualized image.

Figure 7:
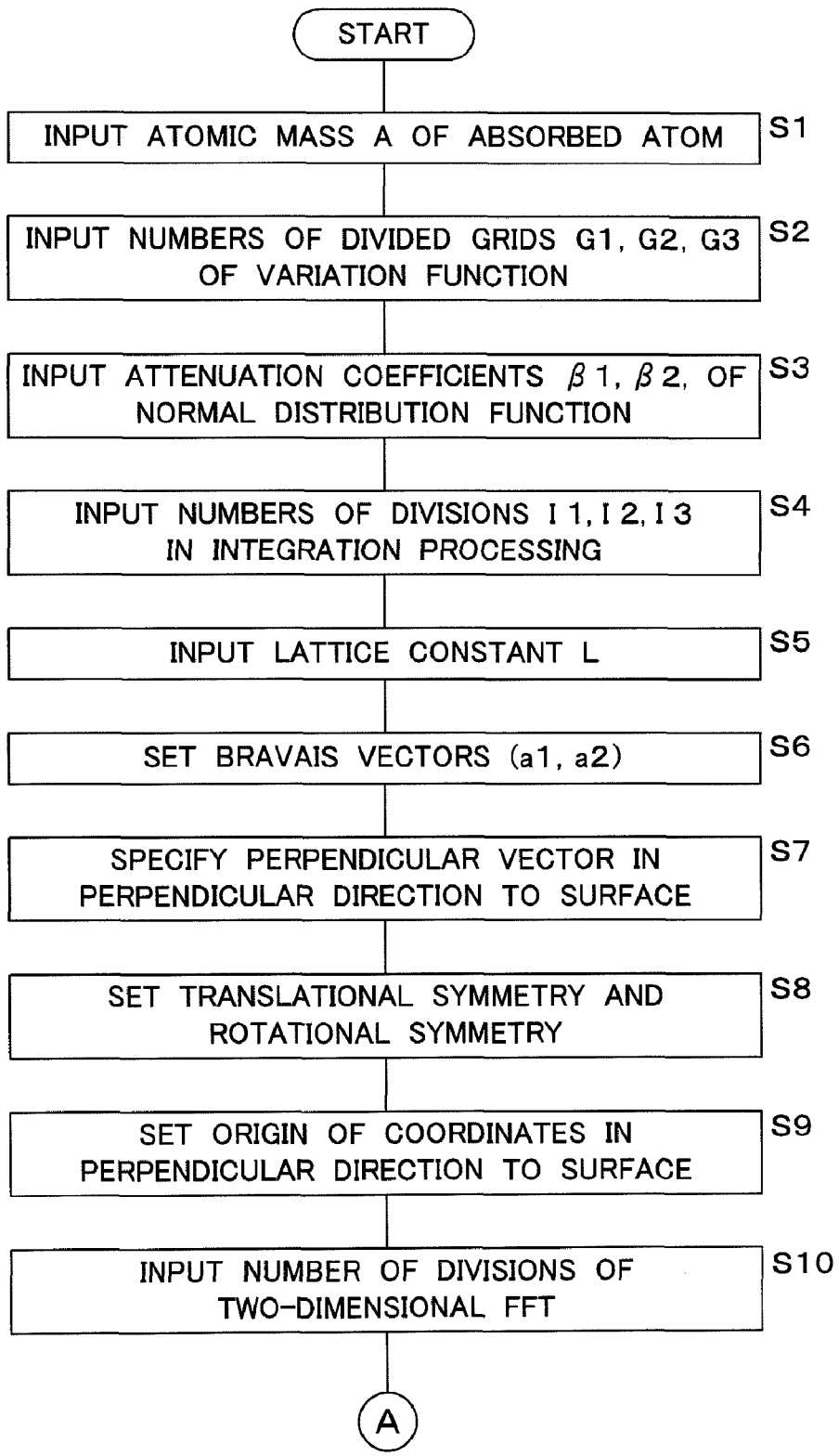
FIG. 7 is a flowchart showing a processing procedure of the quantum state estimation device according to the present invention.
Figure 8:
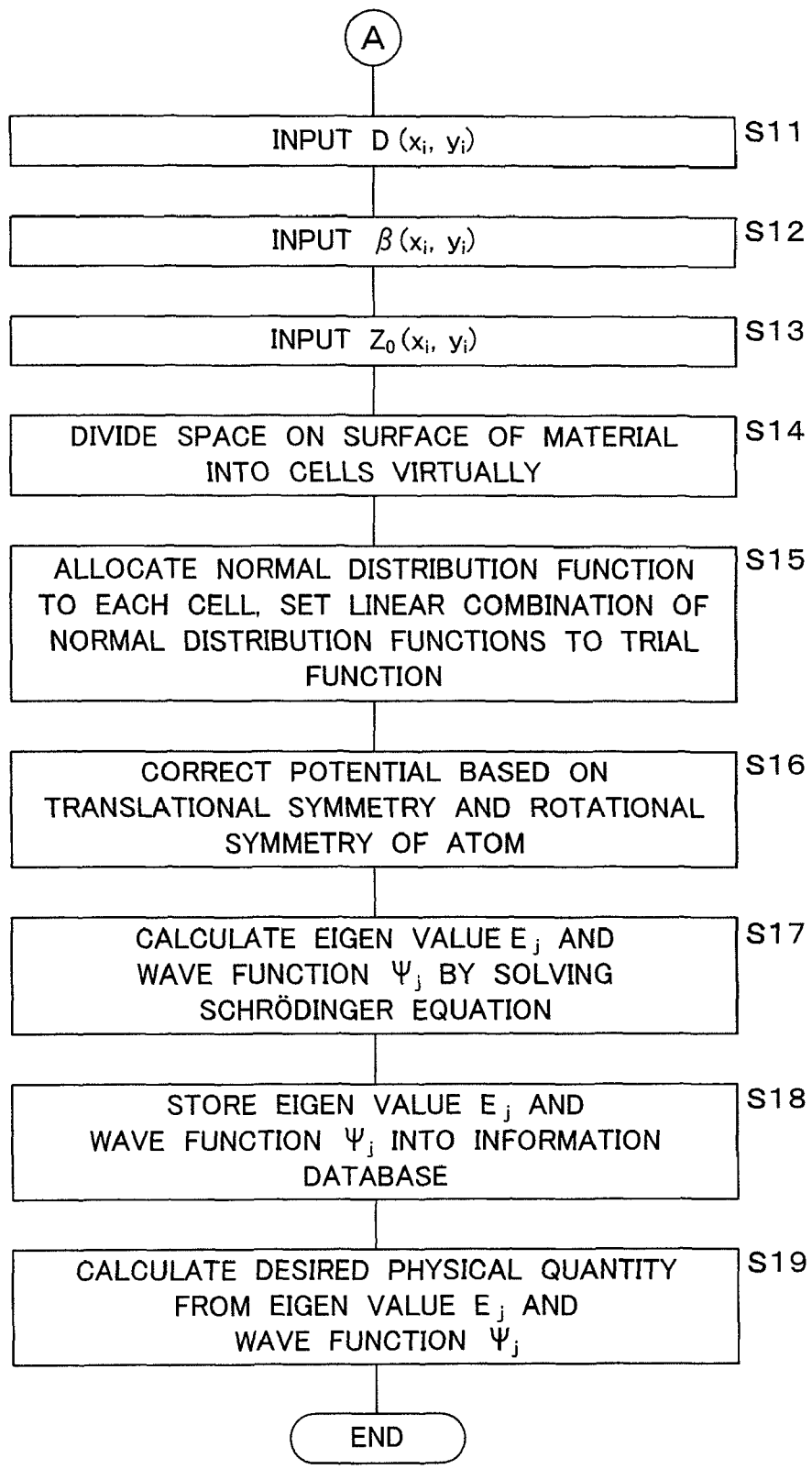
FIG. 8 is a flowchart showing a processing procedure of the quantum state estimation device according to the present invention.

FIGS. 7 and 8 are flowcharts showing a processing procedure of the quantum state estimation device according to the present invention.

First, the quantum state estimation device accepts an input of an atomic mass A of an adsorbed atom by the user (Step S1). Subsequently, inputs of the numbers of divided grids G1, G2 and G3 of a variation function are accepted (Step S2). The numbers of divided grids G1 and G2 correspond to Bravais vectors in the parallel directions to the adsorption surface, and the number of divided grids G3 corresponds to a perpendicular vector in the perpendicular direction to the adsorption surface. It is to be noted that the number of divided grids of the variation function is not necessarily made the same as the number of divided grids at the time of inputting a potential.

Subsequently, inputs of attenuation coefficients 131 and P2 of a normal distribution function (=three-dimensional Gaussian function) for use in the variation function are accepted (Step S3). The attenuation coefficient 131 corresponds to the parallel direction to the adsorption surface, and the attenuation coefficient β2 corresponds to the perpendicular direction to the adsorption surface. It is to be noted that the attenuation coefficients β1 and β2 are set such that the normal distribution functions of the adjacent grids can be overlapped.

Under the above-mentioned conditions, a Hamiltonian matrix element is obtained, and inputs of the numbers of divisions I1, I2, and I3 in integration processing that is executed at the time of obtaining the element are accepted (Step S4). The numbers of divisions I1 and I2 correspond to Bravais vectors in the parallel direction to the adsorption surface, and the number of divisions I3 corresponds to a perpendicular vector in the perpendicular direction to the adsorption surface.

Next, an input of the lattice constant L is accepted (Step S5). In the present example, the lattice constant L is inputted in units of Å, and the inputted lattice constant L becomes a unit in later-described setting of a Bravais vector and a perpendicular vector. Bravais vectors (a1-vector and a2-vector) in the parallel direction to the surface are set (Step S6). Further, a perpendicular vector in the perpendicular direction to the surface is specified (Step S7). The perpendicular vector corresponds to a range of a space as an object for calculation. It is to be noted that the unit in S6 and S7 is the lattice constant L set in S5.

Subsequently, translational symmetry and rotational symmetry are set (Step S8), and an origin of coordinates in the perpendicular direction to the surface is set (Step S9). This origin of coordinates is inputted with a distance from the adsorption surface in units of Å. Then, an input of the number of divisions of two-dimensional Fast Fourier transformation (FFT) is accepted (Step S10), and the characteristic parameters $D(x_i, y_i)$, $\beta(x_i, y_i)$ and $Z_0(x_i, y_i)$ of the potential hypersurface are used for complementing a potential at an arbitrarily point (x, y) other than a grid point by Fourier series expansion.

Then, an input of $D(x_i, y_i)$ is accepted (Step S11). $D(x_i, y_i)$ corresponds to a division point $(x_i, y_i)$ in the parallel direction to the adsorption surface, and for example, when the number of divisions in the parallel direction to the adsorption surface is 8×8, inputs of 64 of $D(x_i, y_i)$ are accepted. Further, an input of $\beta(x_i, y_i)$ is accepted (Step S12). $\beta(x_i, y_i)$ corresponds to the division point $(x_i, y_i)$ in the parallel direction to the adsorption surface, and for example, when the number of divisions in the parallel direction to the adsorption surface is 8×8, inputs of 64 of $\beta(x_i, y_i)$ are accepted. Moreover, an input of $Z_0(x_i, y_i)$ is accepted (Step S13). $Z_0(x_i, y_i)$ corresponds to the division point $(x_i, y_i)$ in the parallel direction to the adsorption surface, and for example, when the number of divisions in the parallel direction to the adsorption surface is 8×8, inputs of 64 of $Z_0(x_i, y_i)$ are accepted.

It is to be noted that $D(x_i, y_i)$, $\beta(x_i, y_i)$ and $Z_0(x_i, y_i)$ that decide the Morse potential can be calculated by obtaining a potential energy hypersurface by means of the first principles calculation based on the density functional method, and then fitting the obtained potential energy hypersurface to the Morse potential. It should be noted that a file in which the above-mentioned data are described may be created and the created file may be processed as an input file.

As thus described, when the above-mentioned data are inputted, the quantum state estimation device virtually divides the space on the surface of the material into cells as calculation units (Step S14). Then, a three-dimensional normal distribution function is allocated to each divided cell, and a linear combination of the normal distribution functions allocated to all cells is set to a trial function (Step S15).

Subsequently, based upon translational symmetry and rotational symmetry of an atom on the surface of the adsorbing material, a potential is corrected (Step S16), and a Schrödinger equation based upon the potential on the surface of the material is solved by a numerical variational method with respect to the set trial function, to calculate an eigen value $E_j$ and a wave function $\Psi_j$ (Step S17).

The calculated eigen value $E_j$ and the wave function $\Psi_j$ are then stored into information database 15 (Step S18). The eigen value $E_j$ and the wave function $\Psi_j$ stored into the information database 15 are read, and a desired physical quantity is calculated from the read eigen value $E_j$ and wave function $\Psi_j$ (Step S19).

For example, when a ground state of an atom or a molecule that is adsorbed is wished to be grasped, an eigen value $E_0$ and a wave function $\Psi_0$ in the ground state have only to be selected and read, and a physical quantity in the ground state has only to be calculated from the read eigen value $E_0$ and wave function $\Psi_0$. Further, in the case of calculating energy that is radiated in state transition from the excited state to the ground state, an eigen value $E_0$ in the ground state and an eigen value $E_j$ (j≠0) in the excited state have only to be selected and read, and the read eigen value $E_0$ has only to be subtracted from the read eigen value $E_j$ (eigen value $E_j$ □ eigen value $E_0$), so that radiation energy can be easily obtained.

EXAMPLE 1

Next, an example is described in which the quantum state estimation device according to the present invention is used when the adsorbed atom being a hydrogen atom and the adsorbing material being platinum (111). Since a quantum effect of the hydrogen atom with a small mass appears remarkably, the hydrogen atom is preferred for confirming the propriety of a calculated wave function.

Based upon a wave function calculated by the quantum state estimation device according to the present invention, a quantum state of the hydrogen atom on the surface of platinum (111) was calculated, and a momentum distribution in the ground state was inspected.

Figure 9:
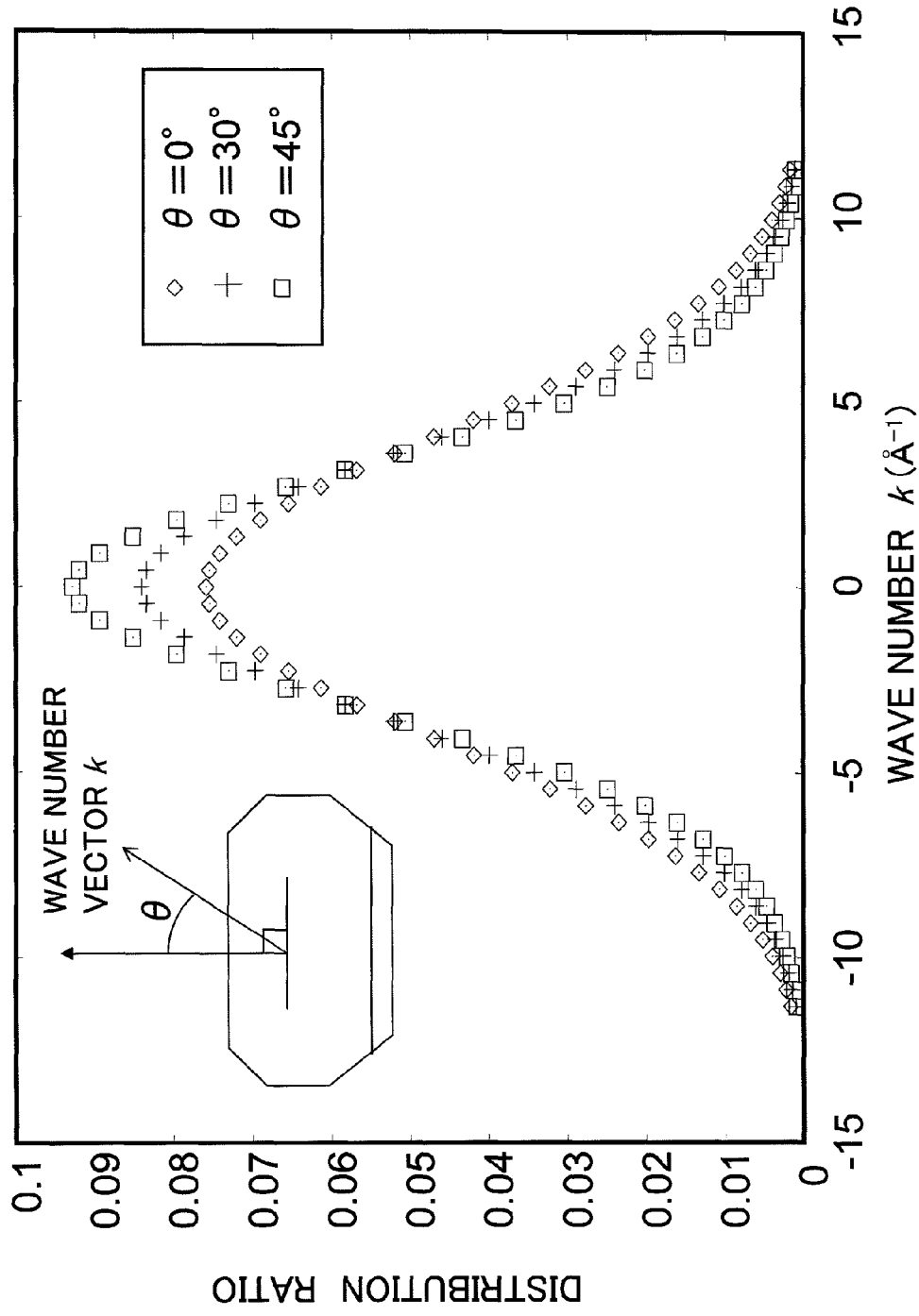
FIG. 9 is an image showing a momentum distribution of a hydrogen atom in a ground state on a surface of platinum (111).

FIG. 9 is an image showing the momentum distribution of the hydrogen atom in the ground state on the surface of platinum (111), and it is expressed using wave number vectors. In FIG. 9, an abscissa axis denotes a wave number $\kappa(\text{Å}^{-1})$, and an ordinate axis denotes a distribution ratio. As shown in FIG. 9, since the momentum distribution of the hydrogen atom in the ground state is displayed as an image in the display section 14, the user can easily grasp the distribution.

In addition, for the purpose of estimating the propriety of the momentum distribution, a comparison was made with a result of an experiment by a resonant nuclear reaction using a tandem accelerator, and it was confirmed that the momentum distribution calculated using the quantum state estimation device according to the present invention agrees with the momentum distribution measured by the experiment.

EXAMPLE 2

Further, a vibration spectrum of an absorbed atom obtained by an electron energy-loss spectroscopy (EELS) has only to be obtained by calculating a difference in eigen value energy between the ground state and the vibrational excited state. It is to be noted that the excited state captured by the EELS is only a vibration component in the perpendicular direction to the surface in the case of the metal surface. It is therefore necessary to find an excited state that can be captured by the EELS. For finding such an excited state, a space distribution of a wave function in the excited state has only to be observed, a wave function having a node in the perpendicular direction to the surface is searched, and a vibration spectrum has only to be calculated based upon an eigen value corresponding to the searched wave function.

Generally, it is extremely difficult to specify the quantum state of the hydrogen atom or the like on the surface of a solid by an experiment, but as shown in each of the examples, the application of the present invention enables highly accurate calculation of a momentum distribution and vibration spectrum. Hence an adsorption site, a vibration mode and the like can be estimated based upon the calculated information, which is extremely effective in development of a catalyst associated with hydrogen, and research and development of surface treatment and the like.

It is to be noted that a configuration is described in the embodiment where the control section 10 reads the computer program 50 previously stored in the ROM 11 so that functions as the quantum state estimation device are carried out, but the control section 10, the ROM 11, the RAM 12 and the like may be realized by an electronic circuit such as a microcomputer, and the functions may be carried out in the form of hardware.

Figure 10:
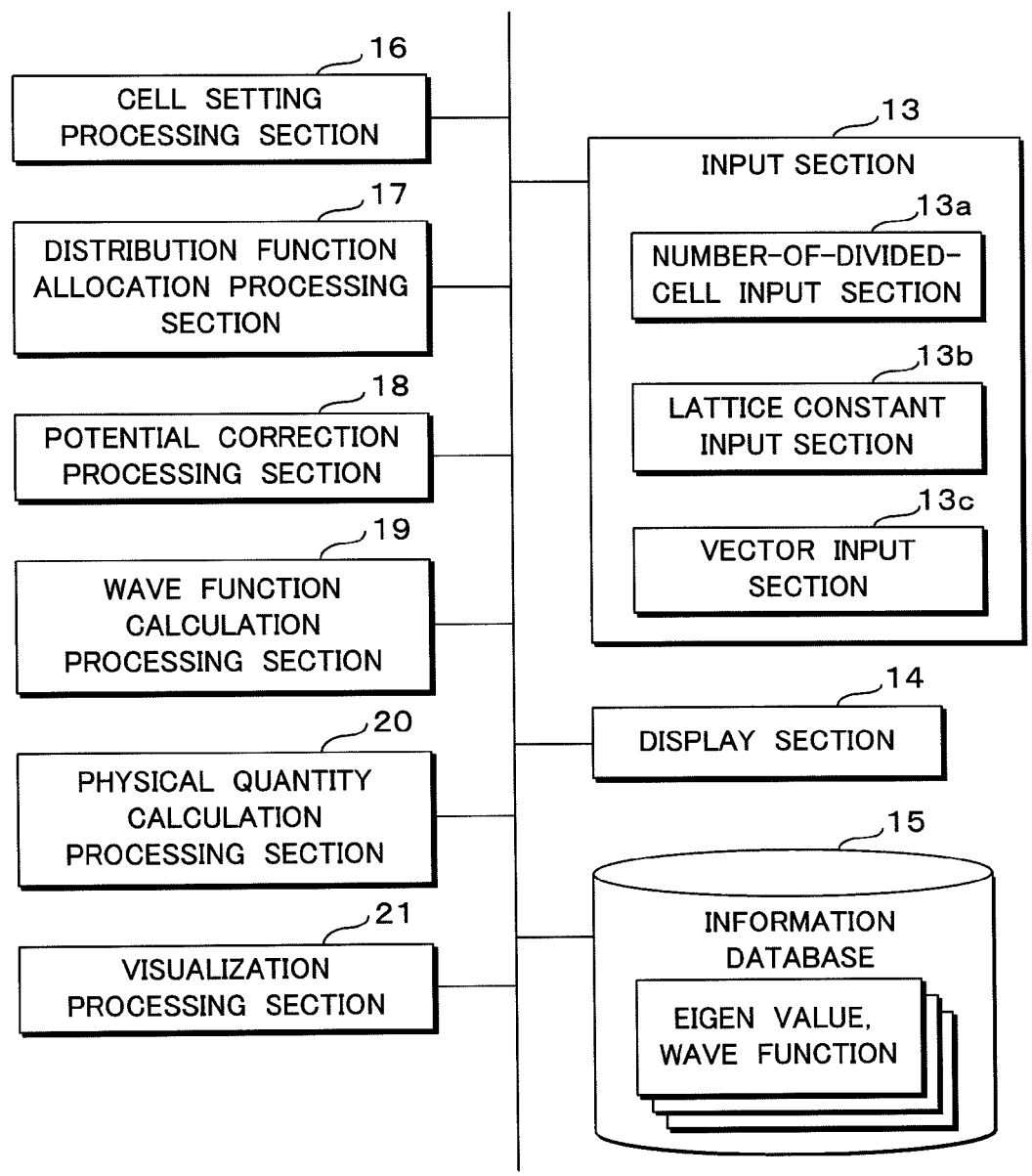
FIG. 10 is a block diagram showing another configuration of the quantum state estimation device according to the present invention.

For example, as shown in FIG. 10, the quantum state estimation device may be the device where the following sections are realized in an electronic circuit: a cell setting processing section 16 that virtually divides a space on the surface of an adsorbing material into cells in accordance with the number of cells, a lattice constant L of the adsorbing material, a Bravais vector and a perpendicular vector, accepted in the input section 13; a distribution function allocation processing section 17 that allocates a three-dimensional normal distribution function to each cell divided by the cell setting processing section 16 and sets a linear combination of the normal distribution functions allocated to all cells to a trial function; a potential correction processing section 18 that performs processing for correcting a potential based upon translational symmetry and rotational symmetry of an atom on the surface of the adsorbing material; a wave function calculation processing section 19 that solves a Schrödinger equation based upon the potential on the surface of the material by a numerical variational method with respect to the set trial function, to calculate a wave function; a physical quantity calculation processing section 20 that calculates a physical quantity for specifying a quantum state based upon the calculated wave function; and a visualization processing section 21 that visualizes the calculated physical quantity.

The present invention is available for a quantum state estimation device. It is particularly available for a preferable quantum state estimation device in a case where hydrogen, lithium, or the like with a small mass, interacts with a solid surface. Such a quantum state estimation device is applicable to the development of a material for a fuel cell, a hydrogen storage material, a hydrogen transmitting material, a material for a lithium-ion (rechargeable) battery, and the like.

The invention claimed is:

1. A quantum state estimation method for estimating quantum states of an atom or a molecule adsorbed on a surface of a material based upon a potential on the surface of the material, comprising the steps of:
   virtually dividing the surface of the material into a plurality of divided regions;
   allocating a normal distribution function to each of the divided regions;
   correcting the potential based upon translational symmetry or rotational symmetry of the atom or molecule on the surface of the material;
   solving a Schrodinger equation based upon the corrected potential by a numerical variational method with a linear combination of the normal distribution functions allocated to all of the divided regions as a trial function, to calculate a wave function; and
   estimating the quantum state of the atom or molecule based upon the calculated wave function.

2. The quantum state estimation method according to claim 1, wherein the correcting of the potential is based upon translational symmetry and rotational symmetry of the atom or molecule on the surface of the material.

3. The quantum state estimation method according to claim 1, further comprising the steps of:
   assuming a Morse potential type in the perpendicular direction to the surface as the potential; and
   calculating structural parameters of the Morse potentials at positions where a center of each divided region is projected to the surface.

4. The quantum state estimation method according to claim 1, further comprising the step of deciding a divided region in which the surface of the material is divided based upon an array periodicity of an atom constituting the material.

5. A quantum state estimation device for estimating a quantum state of an atom or a molecule adsorbed on a surface of a material based upon a potential on the surface of the material, comprising a controller capable of:
   virtually dividing the surface of the material into a plurality of divided regions;
   setting a linear combination of normal distribution functions with respect to all of the divided regions to a trial function;
   correcting the potential based upon translational symmetry or rotational symmetry of the atom or molecule on the surface of the material; and
   solving a Schrödinger equation based upon the corrected potential by a numerical variational method on the basis of the set trial function, to calculate a wave function.

6. The quantum state estimation device according to claim 5, wherein said controller is further capable of correcting the potential based upon translational symmetry and rotational symmetry of the atom or molecule on the surface of the material.

7. A quantum state estimation device for estimating a quantum state of an atom or a molecule adsorbed on a surface of a material based upon a potential on the surface of the material, comprising:
   means for virtually dividing the surface of the material into a plurality of divided regions;
   means for setting a linear combination of normal distribution functions with respect to all of the divided regions to a trial function;
   means for correcting the potential based upon translational symmetry or rotational symmetry of the atom or molecule on the surface of the material; and
   means for solving a Schrödinger equation based upon the corrected potential by a numerical variational method on the basis of the set trial function, to calculate a wave function.

8. The quantum state estimation device according to claim 7, further comprising means for correcting the potential based upon translational symmetry and rotational symmetry of the atom or molecule on the surface of the material.

9. A non-transitory recorded medium readable by a computer and storing a computer program for causing a computer to estimate a quantum state of an atom or a molecule adsorbed on a surface of a material provided with a lattice constant based upon a potential on the surface of the material, said computer program performing the steps of:
   causing the computer to virtually divide the surface of the material into a plurality of divided regions based upon the lattice constant;
   causing the computer to allocate a normal distribution function to each of the divided regions;
   causing the computer to set a linear combination of normal distribution functions allocated to all of the divided regions to a trial function;

causing the computer to correct the potential based upon translational symmetry or rotational symmetry of the atom or molecule on the surface of the material; and causing the computer to solve a Schrödinger equation based upon the corrected potential by a numerical variational method on the basis of the set trial function, to calculate a wave function.

10. The non-transitory recorded medium according to claim 9, wherein the correcting of the potential is based upon translational symmetry and rotational symmetry of the atom or molecule on the surface of the material.

11. The non-transitory recorded medium according to claim 9, said computer program further performing the step of causing the computer to calculate a physical quantity for specifying the quantum state based upon the wave function.

12. The non-transitory recorded medium according to claim 11, wherein the wave functions are a plurality of functions corresponding respectively to a plurality of eigen values, and said computer program further performing the steps of:

causing the computer to store the plurality of functions; and causing the computer to select and read a function required for calculating the physical quantity out of the plurality of functions.

13. The non-transitory recorded medium according to claim 11, said computer program further performing the step of causing the computer to visualize the physical quantity.

* * * * *